US008907275B1

(12) United States Patent
Vidal-de-Miguel et al.

(10) Patent No.: US 8,907,275 B1
(45) Date of Patent: Dec. 9, 2014

(54) METHOD AND APPARATUS TO IMPROVE THE SEPARATION CAPACITY IN A SEQUENCE OF ION FILTERS INCORPORATING AT LEAST TWO ION MOBILITY ANALYZERS

(71) Applicant: Sociedad Europea de Analisis Diferencial de Movilidad, Madrid (ES)

(72) Inventors: Guillermo Vidal-de-Miguel, Madrid (ES); Miriam Macia, Madrid (ES)

(73) Assignee: Sociedad Europea de Analisis Diferencial de Movilidad, Madrid (ES)

( * ) Notice: Subject to any disclaimer, the term of this patent is extended or adjusted under 35 U.S.C. 154(b) by 0 days.

(21) Appl. No.: 14/282,140

(22) Filed: May 20, 2014

Related U.S. Application Data

(60) Provisional application No. 61/825,109, filed on May 20, 2013.

(51) Int. Cl.
H01J 49/04 (2006.01)
H01J 49/36 (2006.01)
H01J 49/00 (2006.01)
G01N 27/62 (2006.01)

(52) U.S. Cl.
CPC .......... *H01J 49/004* (2013.01); *H01J 49/0031* (2013.01); *H01J 49/0422* (2013.01); *G01N 27/622* (2013.01)
USPC ........... 250/290; 250/281; 250/282; 250/287; 250/288; 250/293; 250/295; 250/299

(58) Field of Classification Search
CPC .............. G01N 27/624; G01N 27/622; G01N 30/7206; H01J 49/04; H01J 49/004; H01J 49/0031; H01J 41/00; H01J 41/36
USPC ......... 250/281, 282, 283, 287, 288, 290, 293, 250/295, 299
See application file for complete search history.

(56) References Cited

U.S. PATENT DOCUMENTS

| | | | | |
|---|---|---|---|---|
| 7,579,589 B2 * | 8/2009 | Miller et al. | | 250/292 |
| 7,714,284 B2 * | 5/2010 | Miller et al. | | 250/295 |
| 7,812,305 B2 * | 10/2010 | Miller et al. | | 250/287 |
| 8,067,731 B2 * | 11/2011 | Matyjaszczyk et al. | | 250/295 |
| 8,242,442 B2 * | 8/2012 | Krueger et al. | | 250/288 |
| 8,378,297 B2 * | 2/2013 | Vidal-De-Miguel | | 250/290 |
| 8,384,024 B2 * | 2/2013 | Miller et al. | | 250/288 |
| 2005/0167583 A1 * | 8/2005 | Miller et al. | | 250/290 |
| 2008/0149824 A1 * | 6/2008 | Miller et al. | | 250/287 |
| 2010/0320375 A1 * | 12/2010 | Renner | | 250/282 |
| 2011/0133076 A1 * | 6/2011 | Miller et al. | | 250/287 |
| 2013/0306858 A1 * | 11/2013 | Giles et al. | | 250/283 |

* cited by examiner

*Primary Examiner* — David A Vanore
(74) *Attorney, Agent, or Firm* — Hoffmann & Baron, LLP

(57) ABSTRACT

A method and an apparatus are described to improve the separation capacity of an ion analyzer incorporating at least two stages of ion mobility analysis. The new invention utilizes possible use of different mixtures of gases and dopants in each stage, control over different concentrations of gases and dopants in each stage, and allowance of passage of the selected ions from one stage to the next while avoiding the mixing of the gases and dopants among stages. The new invention also includes a method to reduce the time required to identify the physical properties in a set of ion filters where at least one of the filters is a scannable ion mobility analyzer. The present invention also includes how to provide a set of scannable ion mobility analyzers operating in series, wherein each stage can be operated as a filter, or allowing for the passage of all ions.

13 Claims, 8 Drawing Sheets

METHOD AND APPARATUS TO IMPROVE THE SEPARATION CAPACITY IN A SEQUENCE OF ION FILTERS INCORPORATING AT LEAST TWO ION MOBILITY ANALYZERS

CROSS-REFERENCE TO RELATED APPLICATION

This application claims priority to U.S. Provisional Patent Appl. No. 61/825,109, filed May 20, 2013, the entire contents of which are incorporated by reference herein.

FIELD OF THE INVENTION

The invention relates to an improved method and apparatus to detect known species, and to measure the physical properties of species, where at least two stages of ion mobility filters are utilized in series. More specifically, the invention teaches how to improve the separation capacity of the resulting instrument by increasing the orthogonality of the mobility measurements by selectively introducing dopants in at least one of said stages, and how to reduce the time required to measure the physical properties of said species in a set of filters operating in series and where at least one scannable ion mobility analyzer is utilized.

BACKGROUND OF THE INVENTION

Ion Mobility Spectrometry (IMS) followed by Mass Spectrometry (MS) analysis is an emerging and very powerful technique that provides extra structural information, and an increased resolving power, both these features being very useful in the fields of -omic, which include metabolomics studies, proteomic studies and other biological analysis, and petroleomic studies, as shown by different studies[1-5]. There are, to date, different IMS approaches:

1) Drift Time IMS (DT-IMS)[6] is one of the best known mobility techniques, perhaps due to its simplicity, robustness, speed, and relatively small size and power consumption. DT-IMS are mostly used for military and security purposes[7], although they are also used in other industries as well as in many new areas of research including proteomics and structural biology[8-11]. The resolving power of DTIMS (R) is mainly limited by Brownian diffusion; classic DT-IMS can reach R=100, but their sensitivity is limited by a low duty cycle. Nevertheless, their transmission can be improved by the use of ion funnels[12], multiplexing and ion accumulation[13]. Resolving powers higher than 300, and approaching 400, were achieved with the so-called High-Resolution Ion Cyclotron Mobilityl[14,15]. The pulsed input and output of DT-IMS might be advantageous if the ion source is also pulsed, but it usually hinders transmission and complicates the interfaces in tandem schemes, such as IMS-MS, and with other continuous ion sources such as electro-spray (ESI).

2) Travelling Wave IMS (TW-IMS): Its separation mechanism allows for true mobility separation, but in practice it also produces pulsed packets of ions and, what is more serious, the reliability of the structural information obtained is unclear because: (i) in the intense electrical fields required, ion heating can have a significant effect[16], and (ii) drift time is related to the mobility in a complicated way, which is still not completely understood[17,18].

3) Field Asymmetric IMS (FAIMS)[19-22], also termed Differential Mobility Spectrometry (DMS), is an alternative and robust technique that separates ions in space rather than in time, thus producing a continuous flow of selected ions with a 100% duty cycle. FAIMS separates ions according to non-linearities in the mobility arising in strong fields[23-25], and traditionally produced relatively poor resolving powers (near 20). Nevertheless, recent developments[26-29] have shown that the separation capability can be dramatically increased by adding polar dopants to the drifting gas. Shvartsburg and Smith[30] also reached resolving powers exceeding 200 by increasing the time of residence of ions within the filter. The new generation of DMS-MS commercialized as 'SelexIon' is a powerful tool to reduce background levels[31], and allows mobility selection before ions pass through the Atmospheric Pressure Ionization (API) interface[32], which permits the incorporation of the IMS by a relatively simple upgrade of the MS (if compared with TW-IMS that require low pressures), but it does not provide clearly interpretable structural information.

4) Differential Mobility Analysis (DMA) provides absolute mobility analysis, and also produces a continuous output of mobility-selected ions. Planar DMAs[33] permit coupling with virtually any API-MS[33] and provide an improved transmission of ions. The mobility is measured at moderated ionic temperatures with little fragmentation, which makes structural interpretation of the data easier[34-37]. However, DMAs require a flow with high speed and high Reynolds numbers (Re) that is prone to turbulence[38].

5) Variable Electric Field Mobility Analysis (VEFMA) US 20100243883 A1 also provides a continuous output of mobility selected ions. Ions are separated according to their true mobility using only electric fields. The selected ions coalesce at the analyzer outlet while other ions are deflected away and not transferred. Ions are separated in space and thus a continuous flow of filtered ions with a narrow range of selected mobility ions is produced, as in Differential Mobility Analyzers (DMAs); yet no high fluid velocity field is required, thus avoiding the limitations in DMAs associated with flow unsteadiness, and turbulent transition. VEFMA is at present the only technology capable of: (i) producing a continuous output of mobility selected ions, (ii) operating at ambient pressure, (these two aspects are essential for the Add-on architectural capability), (iii) selecting the ions according to their absolute mobility, and (iv) being able to operate in transparent mode (i.e. allowing ions of all mobilities to pass though the outlet of the analyzer without being mobility selected).

Tandem IMS-IMS: While IMS is very powerful, tandem IMS-IMS analysis and pre-filtration is also attracting increasing interest. In the general IMS-IMS scheme, two mobility filters are coupled in series, and ions are preselected according to their mobility in the two different stages. As illustrated by the pioneering work by Clemmer's group[39-43], IMS-IMS-MS analysis provides an extra dimension of separation, which increases the total separation capacity[42]. The recent study by Hill's group[44], where a Drift Tube IMS (DTIMS) was coupled with a Synapt MS (from the commercial brand Waters), also illustrates the potential of the (IMS-MS)$^2$ approach. This set-up, for which the outlet of the DTIMS was also gated to pass only one type of mobility selected ions, also shows that, if a high duty cycle is required, it is very desirable to use mobility pre-filter capable of producing a continuous output of mobility selected ions when coupling with pre-existing mass spectrometers.

The use of pulsated output IMS analysis techniques (namely DTIMS and TWIMS) for IMS-IMS analysis has two main problems:

i) the duty cycle of each stage is usually very low (around 1%), and the duty cycle of the composed architecture tends to be even lower (1% times 1%=$10^{-4}$), and this low duty cycle reduces the sensitivity of the analyzers.

ii) Coupling the two pulsed IMS stages requires a complicated synchronization to gate the desired pulse of ions in the second stage at the time when they arrive at the outlet of the first stage, which is not known a priori.

For these reasons, it is more desirable to use mobility filters that produce a continuous output of selected ions, such as FAIMS, DMA, and VEFMA. Although these technologies are historically grouped together, a main aspect differentiates FAIMS from DMA and VEFMA: FAIMS measures the variation rate of the ion mobility at increasing electric fields (it does not measure the mobility of the ions), while DMA and VEFMA measure the absolute mobility of the ions (defined as the ratio of electric velocity to electric field).

Tandem DMA-DMA: The use of tandem DMA systems is described by F. de la Mora et. al. in U.S. Pat. No. 7,855,360 and in its continuation patent U.S. Pat. No. 8,278,622. In this invention, F. de la Mora describes how to operate at least one DMA in tandem with other ion filters, and he highlights the advantage of using various filters in series, including at least a DMA, in which the DMA provides a continuous output of mobility selected ions. In the type of configurations described by F. de la Mora, the sensitivity for targeted ions can be much better than that achievable by traditional IMS in tandem with mass spectrometry approaches (namely, DT-IMS in tandem with MS) because each ion can be monitored with a very high duty cycle. F. de la Mora proposes various approaches to the pre-filtration of ions in two DMA in tandem, which are relevant to the present invention: (i) By operating each DMA at different speeds, the invention of U.S. Pat. Nos. 7,855,360 and 8,278,622 allows the mobility to be measured at different electric field strengths, which, as described by F. de la Mora, allows the separation capacity of the tandem DMA-DMA architecture to be increased. Alternatively, the invention of de la Mora also incorporates using two DMA in tandem, and additional means to change (by attachment of vapor molecules, or by fragmentation, or by oxidation) the ions after being analyzed in the first DMA, and before entering in the second DMA. This approach was previously used by McMurry and colleagues at U. Minnesota[4,5] for the analysis of aerosols, but F. de la Mora extended the concept to the analysis of ions.

The architecture described in U.S. Pat. Nos. 7,855,360 and 8,278,622 allows for the detection of one or several target ions within a mixture of ions with high resolution. However, when the filtering parameters of each DMA are not known a priori, which is a very common circumstance if the operator wishes to identify these variables, or if the operator wishes to re-calibrate the instrument, all the DMA stages must be scanned together in a multi-dimensional spectrum because they cannot operate in transparent mode, and this scan can be very time consuming. The typical identification of the filtration parameters in a triple quadrupole comprises the following steps: (i) in order to calibrate the first quadrupole, a known amount of substance is introduced into the instrument by the operator, the third quadrupole is operated in transparent mode (allowing the passage of all ions), the first quadrupole is scanned so as to produce a spectrum, and the mass of the precursor ion is identified in this first spectrum. Once the precursor ion is identified, in a second step (ii), the first quadrupole is operated to pass only the selected precursor ions, and the second quadrupole is scanned so as to produce a spectrum, which is used to identify the masses of the product ions. This procedure is relatively quick because the two spectra are one-dimensional (meaning that only one parameter is scanned at a time). If each spectrum is composed of 1000 positions of the corresponding filtration parameter, and the measurement of each position takes 50 ms, the time required to identify the filtering parameters in each quadrupole would then be 100 seconds, and the total time for two of these filters capable of operating in transparent mode would be less than 2 minutes. The equivalent procedure in the case of including a DMA and a triple quadrupole takes much longer because the DMA cannot be operated in transparent mode, the identification of the precursor ion requires a two-dimensional scan of the DMA and the first quadrupole, in which the third quadrupole can be operated in transparent mode. If each DMA scan requires 200 points (which are required to have at least four points per peak-width for a resolving power of 50), and the quadrupole scan requires 1000 points, each taking 50 ms, the time required to perform the required double scan is 200×1000×50 ms=10000 seconds (approximately two and a half hours). In an architecture comprising only two DMAs in tandem and a detector requiring 50 ms to measure the signal produced at each point of the spectrum, the time required to identify the position of the peak would be 200×200×50 ms=2000 seconds (slightly more than half hour). The time required to identify the position of the peaks in a DMA-DMA-quadrupole architecture would be simply prohibitive (approximately three weeks).

These times are not a big problem if the system is used to detect species which are previously known. For instance, the architecture can be used in an explosive detector, for which the filtering parameters are not expected to change (aside from fine tuning), but these high times become a real problem if the architecture is to be used in a more general purpose platform for which identification of the filtrating parameters can be a regular procedure. Accordingly, one objective of the present invention is to teach how to operate a set of ion filters, in which at least one of them is and ion mobility filter, and in which at least one of said ion filters can be operated in transparent mode (allowing the passage of all ions) so as to reduce the time required to identify the peaks of the species of interest.

Having a good transmission is important if the user wishes to detect species for which their properties (and hence the position of the peaks in the spectra) are previously known. For instance, if the two DMA in tandem are to be coupled with a mass spectrometer as described in U.S. Pat. Nos. 7,855,360 and 8,278,622. On the other hand, the possibility to operate in transparent mode (allowing all ions to be transferred together irrespectively of their mobility), which is offered by the VEFMA, provides a higher flexibility and shorter peak identification times, which greatly facilitates the identification of the peaks in the stages of analysis by reducing the time required to complete the identification (from 2 hours to 3 minutes).

The invention described in U.S. Pat. Nos. 7,855,360 and in 8,278,622 also has the problem that transmission of ions between one DMA and the next is very poor. Each DMA requires a laminar and high speed flow (with high Reynolds and high pressure gradients) to separate the ions, and these flows are very delicate because they easily become turbulent due to their high Reynolds. This problem can be solved by means of using very carefully designed DMA drift flow channels, which remain laminar at very high Reynolds by maintaining the boundary layer of the DMA flow constantly accelerated and unperturbed. However, the strong pressure gradients produced by the high speed flow tend to deform the inner walls of the DMA, and these deformations affect the boundary layer of the flow, which might easily become turbulent, thus destroying the resolving power of the DMA. A solution to this problem is explained by Rus et al. (See US 20080251714), where a rigid structure is used to minimize deformations and to ensure that the whole structure is gas tight, such that the boundary layer in a DMA remains unperturbed. Rus also teaches how to transfer the ions from the DMA to a mass spectrometer, where the ions are directed towards the MS by the gas that passes from the DMA toward the vacuum side of the MS at very high speeds, as they are suctioned by the vacuum of the MS. However, if the rigid structure of US 20080251714 is used in combination with the tandem DMA-DMA architectures proposed in U.S. Pat. Nos. 7,855,360 and in 8,278,622, then the transmission of ions would be very poor for two main reasons:

(i) in a tandem DMA-DMA scheme, the local pressure gradient that pushes the gas and the ions from one DMA to the next cannot be very high, because the flow of incoming gas and ions that pass from one DMA to the next would otherwise form a jet in the second DMA that would perturb the high Reynolds flow of the second DMA, which would become turbulent, and which would thus have a very poor resolving power and a poor transmission. As a results, ions have to be transnsported from one DMA to the next at low velocities, for which diffusional losses dominate.

(ii) the need for thick and rigid structures in each DMA inevitably requires a thick wall between each DMA, which must be crossed by the slit that allows for the passage of ions from one DMA to the next, resulting in a long time of residence of the ions through these slits. These long slits (the slits are long along the direction of the movement of the ions through the slit) also impede the passage of electric fields, which cannot be used to push the ions forward.

As a result, the ion losses in the channel that communicates one DMA with the next are very high. Moreover, if additional means to change (by attachment of vapor molecules, or by fragmentation, or by oxidation) the ions after being analyzed in the first DMA, and before entering in the second DMA are used, the ion losses through said long slits (the slits are long along the direction of the movement of the ions through the slit), and through said additional means become even higher.

Tandem IMS-IMS by Means of a Multi-Stage VEFMA: FIG. 1 illustrates schematically one embodiment of a Two-stages 2D-VEFMA, as described in US 20100243883 A1. This embodiment of the VEFMA is composed of two insulator boxes, the first insulator (1) housing the inlet electrode (2), each insulator box housing two deflector electrodes (3), and the second insulator (4) housing the outlet electrode (5). The intermediate electrode (6) is a thin plate that separates the two stages and allows ions to be transferred through the intermediate slit (7). In contrast with the DMA-DMA architecture, the pressure gradients in the VEFMA are very low, and this allows the intermediate electrode (6) to be very thin. As a result, the ions can be transmitted through the slit (7) by the local electric fields that easily pass through the slit. The outlet electrode incorporates a slit (8) which is elongated on the side receiving the selected ions, and which, if required, becomes a rounded orifice on the opposite side of the outlet electrode so as to better fit the inlet of a subsequent analyzer (which can be a mass spectrometer). Ions reaching the outlet slit are directly carried by the flow toward the subsequent analyzer (9), while a counterflow gas (10) exits through the inlet slit (11) so as to prevent droplets from entering the analyzer. The required gases are introduced into each VEFMA chamber through two lateral inlets (12). The voltage required by the inlet electrode (2) is AV1, the voltage of the intermediate electrode (6) is AE2, and the voltage of the outlet electrode (5) is AV3. The Deflector Electrode (3) voltages are DV1 through DV4 (DV1 and DV2 in the first stage (1), and DV3 and DV4 in the second stage (4)).

The usefulness of the analysis of the mobility of the ions in two consecutive stages, which in general is measured by the separation capacity of the system, depends on the statistical orthogonality (or dispersion) of the two measurements. If the mobility of the ions in one stage is linked with the mobility in the second gas, then adding the second stage will not increase the separation capacity, whereas the species will be more separated if the mobilities are more orthogonal, and hence the separation capacity of the system will be higher. Note that separation capacity is defined in the context of the present invention as the number of different species that can be differentiated in a spectrum. The separation capacity will thus be higher if the width of the peaks produced by the analyzer is smaller, and it will be also higher if the dispersion of the physical parameters being measured is higher. FIG. 2 illustrates schematically two sets of mobility pairs, in which each point corresponds with the pair of mobilities of a given ion in each mobility measurement stage. In the first case (left, poor orthogonality), the mobilities in the two stages are linked (the dots are not dispersed, meaning that the measurements are not orthogonal). As a result, two different type of ions, which have the same mobility in the first stage, and which thus pass together through the first stage at a given mobility (not being differentiated in the first stage), cannot be differentiated in the second stage because their mobilities in the second stage are also very similar, meaning that the separation capacity of the analyzer is poor. In the second case (right, better orthogonality), the mobilities in the two stages are not linked (the dots are dispersed, meaning that they are highly orthogonal). In this case, although two type of ions, which have the same mobility in the first stage cannot be differentiated in the first stage, they will be differentiated in the second stage. As a result, the separation capacity of the analyzer is much improved. Note here that FIG. 2 is here used to illustrate how the simultaneous measurements of ions in two different mixtures of gases and dopants can improve the separation capacity, even if the peak width is not affected.

In short, in order to achieve a high separation capacity, it is very desirable to have highly orthogonal measurements. This can be done by modifying the ions between one mobility measurement stage and the subsequent mobility measurement in an intermediate modification cell, which resembles the role of the collision cell in triple quadrupoles. For instance, this type of modification can be achieved by means of an ion funnel, which can be located between the two subsequent drift cells, and in which ions are excited prior to entering in the next stage, as described by Clemmer[39,46]. Other approaches, as described in U.S. Pat. Nos. 7,855,360 and 8,278,622, would incorporate means between one stage and the subsequent stage such that ions and charged particles undergo some change after being classified in the first filter and before entering in the second filter.

These means can include attachment of vapor molecules, fragmentation, and oxidation. While these approaches increase the separation capacity, they have a poor transmission of selected ions. This poor transmission is mainly caused due to losses of ions in the required ion modification stage. In order to maximize the transmission, it is desirable to pass the ions directly from the one stage to the next, but this scheme would not provide enough space for the required modification cell. In short, the present state of the art imposes a trade-off between separation capacity/orthogonality, and ion transmission. Accordingly, one objective of the present invention is to provide highly orthogonal mobility measurements with a high transmission of the selected ions.

An attempt to solve this problem is described in US 20100243883 A1, in which it is described that each of the two stages of the 2D-VEFMA can be operated with different gasses, such as $N_2$, which is cheap to produce, or $CO_2$ or $SF_6$, such that the first stage provides the measurement of the mobility in one gas, and the second stage provides a measurement of the mobility in a different gas. This architecture offers a good transmission (the duty cycle is 100%, and the ions can pass from one VEFMA stage to the next stage very quickly). However, experimental data shows that the mobility in the different gases ($N_2$, $CO_2$, $SF_6$) is poorly orthogonal. The orthogonality of the measurements in US 20100243883 A1 is poor, and hence the separation capacity of the tandem IMS-IMS analysis is also poor. Besides, the invention of US 20100243883 A1 does not disclose how to identify the position of the peak in each stage independently. Accordingly, one objective of the present invention is to teach how to identify the filtering parameters of a sequence of ion filters, in which at least one ion filter is an IMS, and in which at least one ion mobility filter is of the type that produces a continuous output of mobility selected ions, and that has the capacity to operate in transparent mode (such as the VEFMA). Also, the invention of US 20100243883 does not teach how to control the concentration of different gasses in each stage, which would vary according to US 20100243883 because each stage is communicated with the next though the intermediate slit (7). This slit is required to allow the ions to pass from one stage to the next, but it also allows the gasses to pass from one stage to another. As a result, the composition of the gasses in each stage is an uncontrolled mixture of different gasses initially introduced each stage, thus leading to non repeatable and difficult to interpret results. Accordingly, one goal of the present invention is to enable the passage of ions from one stage to the next, and to control at the same time the concentration of gasses in each stage.

The Use of Dopants in IMS: The addition of polar and non-polar dopants to the gas through which the mobility of ions is measured serves to modify the mobility of the ions, to enhance the signal produced by some desired ions, and to eliminate the signal produced by some undesired ions. Although the mechanisms by which dopants affect the mobilities of the different type of ions is not well understood, the use of dopants is very common in Drift Tube IMS, as illustrated by multiple patents in the field: U.S. Pat. No. 8,237,110B2, US20120138783A1; U.S. Pat. No. 8,084,000B2; US20110300638A1; US20110297821A1; US20110291000A1; U.S. Pat. Nos. 7,999,224B2; 7,994,475B2; 7,985,949B2; 7,956,323B2; US20110114210A1; US20100308216A1; US20090179145A1; US20090039243A1; US20090032699A1; U.S. Pat. Nos. 5,283,199A; 5,234,838A; 5,095,206A. Note that, in these applications, dopants do not increase the overall separation capacity of the instruments. The dopants have the capacity to shift the position of the peaks in mobility spectra. While these shifts can be helpful to improve the sensitivity for some specific species, or to separate some species from their contaminants in some specific scenarios, dopants can have the opposite effect on other species. For instance, due to its capacity to modify the mobility of the ions, a dopant can be useful to separate two species which would otherwise appear at the same mobility if the dopant was not used. However, other analytes, which are properly separated without the dopants, could appear at the same mobility due to the addition of the dopant. In this second case, the introduction of the dopant would be counterproductive. As a result of this, the selection of the right dopant is very application-specific. And hence, the use of dopants, and the selection of the right dopant require specific studies for each application, and cannot be used by default in a general purpose system. An architecture for which dopants could statistically provide an improved separation capacity regardless of the particular application, and for the majority of species of interest (say more than 10% or 20% or 50% or 70% of the species in a sample) would allow users to incorporate the use of dopants in a general purpose system, and would allow them to minimize the required specific studies. However, there is to our knowledge not a solution to solve this problem. Accordingly, one objective of the present invention is to use dopants to statistically increase the separation capacity (regardless of the particular application) in a sequence of filters, incorporating at least two ion mobility filters, and.

It is noted here that dopants are used to enhance the separation capacity in FAIMS (also termed DMS) (US20100308216A1), where they show that the nonlinear effects on the mobility are highly increased. However, FAIMS do not provide absolute mobility ion selection.

Despite the potential offered by dopants, using them in IMS-IMS applications is very complicated. Very small concentrations of dopants (in the ppm range) can produce a very dramatic change in the mobility of certain ions. While this can be a great advantage to enhance the separation capacity of tandem IMS-IMS schemes, including the combinations of VEFMA and DMA, introducing different dopants in each IMS stage has two main problems:

(1) The gases of the different stages tend to pass from one stage to the other because pressure gradients among the different stages tend to drive gases through the ports intended originally to allow for the passage of the selected ions.

(2) Even if one could eliminate these pressure gradients, trace amounts of the dopants would tend to diffuse and pass from one stage to the other.

As a result of these effects, the concentration of dopants becomes unpredictable and difficult to control. And hence the mobility varies in an uncontrolled fashion, which makes it impossible to take advantage of the use of dopants in IMS-IMS schemes. Accordingly, one objective of the present invention is to control the concentration of dopants in a sequence of ion filters incorporating at least one ion mobility filter.

In conclusion, for the analysis of the mobility in various IMS analyzers operating in series, it is very desirable to be able to:

(i) provide a high resolving power,
(ii) provide a high ion transmission,
(iii) measure the absolute mobility
(iv) provide the possibility to operate each IMS stage in transparent mode, and
(v) utilize mobility measurements in each stage that provide a high orthogonality among stages, and which thus provide an improved separation capacity.

Accordingly, one goal of the present invention is to solve the problem of producing highly orthogonal IMS-IMS measurements with various mobility filters in tandem.

Another objective of the present invention is to accomplish highly orthogonal mobility measurements and a high transmission of the selected ions.

A further objective of the present invention is to increase the separation capacity (regardless of the particular application) in a sequence of filters, incorporating at least two ion mobility filters.

Yet a further objective of the present invention is to accurately control the concentration of dopants in each stage of an ion-separating apparatus, such that the mobility variations can be controllable and predictable.

Also, a further objective of the present invention is to operate a sequence of ion filters, in which at least one of them is an ion mobility filter, and in which at least one of said ion filters can be operated in transparent mode (allowing the passage of all ions) so as to reduce the time required to identify the peaks of the species of interest. This approach is new and it is part of the present invention.

Yet another objective of the present invention is to identify the filtering parameters of a sequence of ion filters, in which at least one ion filter is an IMS, and in which at least one ion mobility filter can be operated in transparent mode. Another objective of the present invention is to identify the filtering parameters of a sequence of ion filters, in which at least one ion filter is an IMS, and in which at least one ion mobility filter of the type that produces a continuous output of selected ions, and which can also operate in transparent mode, including the VEFMA.

SUMMARY OF THE INVENTION

A method and an apparatus are described to filter ions according to their mobility in more than one ion mobility analyzer, wherein a high separation capacity is achieved by selectively using different mixtures of gases and dopants in each mobility filter, which improve the orthogonality of the measurements. Note that, for the purpose of the present invention, the orthogonality of two properties is a statistical property of the measurements. It reflects how the mobilities of a significantly large population of various species of ions are dispersed, and how the two properties are not correlated. In short, a higher orthogonality means that two properties are lesser correlated (with possible no correlation), while a poorer orthogonality means that the two properties are more correlated. On the other hand, separation capacity is a property of analytical instruments. It depends on the width of the peaks produced by the analyzer (or by each of its stages, if the analyzer incorporates more than one stage), on how each property of the species being measured is dispersed, and on the orthogonality of these different measurements. In short, the separation capacity reflects how many species an analyzer can differentiate. The separation capacity can be improved in various different ways; it can be improved by improving the resolving power, or the orthogonality of the properties being measured. In the present invention, the separation capacity is improved by improving the orthogonality of the measurements.

As used herein, an "analyzer" may be a single stage or multi-stage apparatus or system. It is to be understood that the principles discussed herein apply equally to separate analyzers in series, as well as, separate stages of a single apparatus. The terms "stage" and "analyzer" are interchangeable herein.

The present invention also teaches how to minimize the flow of gasses and dopants from one ion mobility analyzer to another by means of incorporating a secondary outlet of gas in each of said ion mobility analyzers and by communicating said secondary outlets with a low pressure drop (below 1 mBar, or below 10 mBar, or below 100 mBar) through a secondary outlet collector, such that the pressure drop between the different ion mobility analyzers is below 1 mBar, or below 10 mBar, or below 100 mBar, and such that the flow of gases and dopants from one of said ion mobility analyzer to another is minimized. For the purposes of the present invention, each of said ion mobility filters can be of the type that produces a continuous output of selected ions, and which can also operate in transparent mode, including, but not limited to, the VEFMA.

The present invention also teaches how to compensate for the diffusion of gasses and dopants through the orifices and tubes, which allow for the passage of ions, and which communicate the different ion mobility analyzers, by means of continuously introducing a flow of new gasses and dopants in each ion mobility though an inlet, which is incorporated in each ion mobility analyzer, and by continuously removing said flow of new gases and dopants through said secondary outlets, such that the gases and dopants within each ion mobility analyzer are continuously renewed.

The present invention also teaches how to control the concentration of dopants in a stream of gas, which can be introduced in each of said ion mobility analyzers, and which can play the role of said flow of new gasses and dopants, by pumping a liquid mixture of dopants through a capillary into a mixer chamber, putting the tip of said capillary in contact with a porous material within said mixer chamber, such that a stain smaller than the total surface of said porous material is produced, wherein said dopants evaporate from the surface of said stain, and wherein said stain reaches a size of equilibrium. As a result, the flow of liquid inputted through said capillary equates the flow evaporated through the surface of said stain, and thus, said concentration of each of said gas and dopant is steady and proportional to the respective volumetric flow ratios of each of said gases and dopants.

The present invention also teaches how to reduce the time required to identify the physical properties of a species of interest in a set of ion filters having N filters, which incorporate M scannable ion mobility (where M is at least one), by operating said scannable ion mobility filters in transparent mode and by scanning the spectra in the rest of ion filters. As a result, the number of dimensions that have to be scanned simultaneously is reduced from N to N−M. Ideally, if N=M, identifying the mobility in said set of M ion mobility analyzers would require M scans of one dimension each, whereas the same identification would require only one scan of M dimensions if no transparent mode was used. Note that, if the scan in each dimension requires P measurements, M scans with one dimension require P·M measurements, while one scan with M dimensions requires $P^M$ measurements (a much higher number, which is very time-consuming).

The present invention also teaches how to provide a set of scannable ion mobility analyzers, wherein at least one of said ion mobility analyzers is a VEFMA, and wherein the oscillating components of the deflector electric field of each VEFMA can be switched off, so that all ions follow a straight line that reaches the outlet of the VEFMA. As a result, all ions can be transferred continuously.

BRIEF DESCRIPTION OF THE DRAWINGS

FIG. 6b is a 3D view of the same spectra

DETAILED DESCRIPTION OF THE INVENTION

Figure 1:
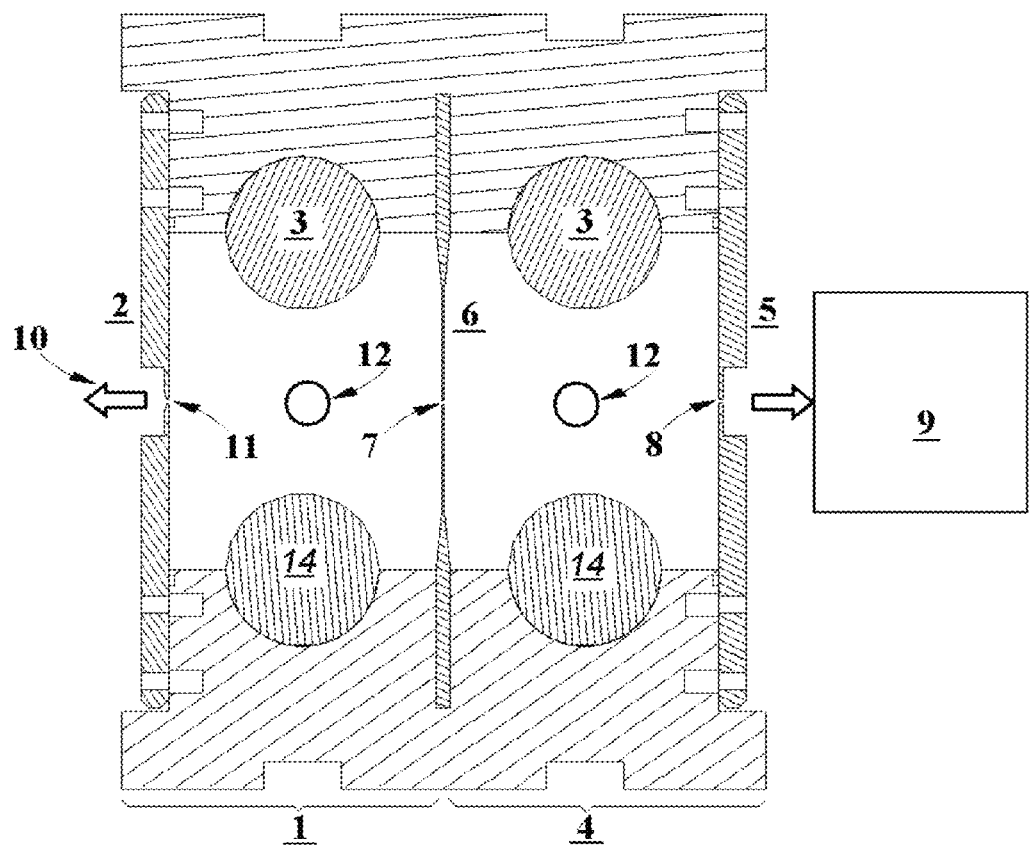
FIG. 1 (Prior art) illustrates schematically one embodiment of a TMIMS (or Two stages 2D-VEFMA), as described in US 20100243883 A1.

In one embodiment of the present invention, analyte ions are produced by means of an ion source operating at pressures above 0.1 Torr. This ion source can be an Electrospray ion source (ESI) (see U.S. Pat. No. 4,531,056 A), a Secondary Electrospray Ion source (SESI) (see US 20100264304 A1, US 20120267548 A1 and US 20100176290 A1), a radioactive ion source, an ionizer utilizing ionization radiation, a corona discharge, a soft plasma ionization source, or any other ion source capable of operating at pressures above 0.1 Torr, which are well known to those skilled in the art.

In the present invention, the ions produced by the ion source are driven toward a sequence of ion analyzers, including at least two ion mobility analyzers, which can be a Drift Tube IMS, a Travelling Wave IMS, a FAIMS, a DMA or a VEFMA. And then ions can be detected by means of an electrometer, or a condensation nucleus counter. Alternatively, ions can be brought to an Atmospheric Pressure Interface (API), and then be further analyzed by means of a Mass Spectrometer (MS).

Multiple Mobility Measurement; Orthogonality Enhancement:

Dopants are widely used in IMS analysis to increase the non-linear effects in FAIMS, and to enhance the signal produced by certain species of interest, but they have not been used to systematically increase the orthogonality of the mobility measurements in tandem mobility analysis. Dopants are chemically specific, which means that their interaction will be very different with different chemical species. For this reason, two species with the same mobility in a neutral gas will usually have different mobilities in a gas incorporating a dopant if it is more prone to interacting with only one of the two species. As an example, if the dopant interacts with acidic substances, and only one of the two species to be analyzed is acidic, then the mobility of the acidic species will be modified more than that of the non acidic species, and the two species will be differentiated.

In one embodiment of the present invention, a sequence of ion filters, which incorporates at least two ion mobility analyzers (which can be a combination of DTIMS, TWIMS, FAIMS, DMA, or VEFMA) is used, where the gas through which the mobility of the ions is analyzed in each ion mobility analyzer is doped with polar and/or non-polar substances (termed dopants in this description of the invention) in order to modify the resulting mobilities. As a result of these modifications produced by the dopants, the orthogonality of the measurements in the ion mobility analyzers is increased, and the overall separation capacity of the sequence of ion analyzers is also increased.

Dopants can interact in many different ways, which are still not fully understood. Some examples of dopants, which are included in the present invention include water vapor, ammonia, halogenated hydrocarbons, nicotinamide, acetone, methanol, ethanol, propanol, or other alcohols including octanol, acidic or basic substances, phenols, substituted phenols, dimethyl methylphosphonate, methyl salicylate, 2-hydroxyacetophenone, $SO_2$, dimetil sulfoxide, 2-chlorobutane, $H_2O_2$, dimethyl methylphosphonate, phosphate esters, ketones, etc. Those skilled in the art will identify other dopants which are useable with the subject invention, such as being used in IMS. In the present invention, these dopants are used to enhance the orthogonality of the mobility measurements in a series arrangement, such as a tandem IMS-IMS architecture, and therefore these dopants are also incorporated in the present invention.

Separation and Control of Said Dopants Concentration in Said Multiple Mobility Measurement System:

Trace concentrations of dopants produce very strong mobility variations. While this is an advantage for the purposes of increasing the orthogonality of the measurements, and hence the separation capacity of the analyzer, it also poses some important problems. In an architecture comprising at least two mobility analyzers, the analyzers must be communicated, usually by means of a channel, orifice, slit or similar, so as to allow ions to pass from one analyzer to the next. However, if ions can pass from one analyzer to the next analyzer, neutral species, including dopants, can also pass from one mobility analyzer to the others. If the flow is at rest, dopants will tend to diffuse from one analyzer to the others, and the situation can be even worse if the drift gas flows from one ion mobility analyzer to the others, or through two drift tubes in series or from a FAIMS to a DTIMS, because the convective velocity of the gas would drive the dopants from one stage to the others. As a result, in conventional tandem IMS-IMS analysis, the concentration of dopants in the different analyzers cannot be controlled. In order to separate the different drift gasses in each mobility analyzer, one embodiment of the present invention utilizes in series FAIMS, DMA or a VEFMA in combination with dopants to enhance the orthogonality of the mobility measurements because these types of mobility analyzers have the advantage that the inlet and the outlet of ions are very small orifices and/or slits, and the passage of dopants through them can be thus minimized.

In order to countermeasure the diffusive dispersion of dopants through the slits or orifices communicating the ion mobility analyzers with the rest of mobility analyzers, another embodiment of the present invention also incorporates an inlet of gas and an extra outlet of gas in each mobility analyzer to allow for the passage of drift gas. The gas and the dopants are thus continuously renewed, and the minute amounts of dopants that would otherwise diffuse through the slits are quickly swept away from each analyzer, such that the concentration of gasses and dopants in each mobility analyzer is constant and equal to that inputted through said inlet of gas. In order to renew the gases and the dopants more efficiently in each stage, the gas can be introduced laterally through an inlet, and it can be evacuated through an outlet located in the opposite side of the analyzer. In particular, in a 2D VEFMA, the flow of gas and dopants can be forced to sweep each stage in a direction parallel to the slits that define the inlet of ions and the outlet of ions. As a result of this particular arrangement, the movement of the flow does not affect the movement of ions in the longitudinal direction nor in the transversal direction, and the renewal of gas and dopants is straight, free from stagnated regions or recirculating regions, and thus it is more efficient. This advantageous flow configuration can be achieved for instance by placing the inlet used to introduce tha mixture of gases and dopants in one of the lateral sides of the VEFMA, in the space between the inlet electrode, the outlet electrode, and the deflector electrode, and by evacuating the gas through the opposing side of the VEFMA stage.

In a series of ion mobility stages or analyzers, in order to prevent the formation of turbulent jets, which would otherwise be produced due to the pressure differences between adjacent stages, which are produced due the continuous passage of the renewed mixture of gasses and dopants in each stage, another embodiment of the present invention also incorporates a series of ion mobility stages, further utilizing dopants so as to enhance the orthogonality and of the mobility measurements and thus to improve the separation capacity of the analyzer, and further comprising secondary outlets of gas in each stage, wherein said secondary outlets have a very low pressure drop (below 10 mBar), and wherein said secondary outlets communicate toward a common outlet collector. This collector of secondary outlets serve to balance the pressure between each stage so as to ensure that no disrupting jets are formed in the intermediate slit. As a result, ions are transferred through the intermediate slits or orifices relying solely on the electric fields, while the gases and dopants in each stage can be continuously renewed, and the passage of gas and dopants from one stage to another is minimized.

Figure 3:
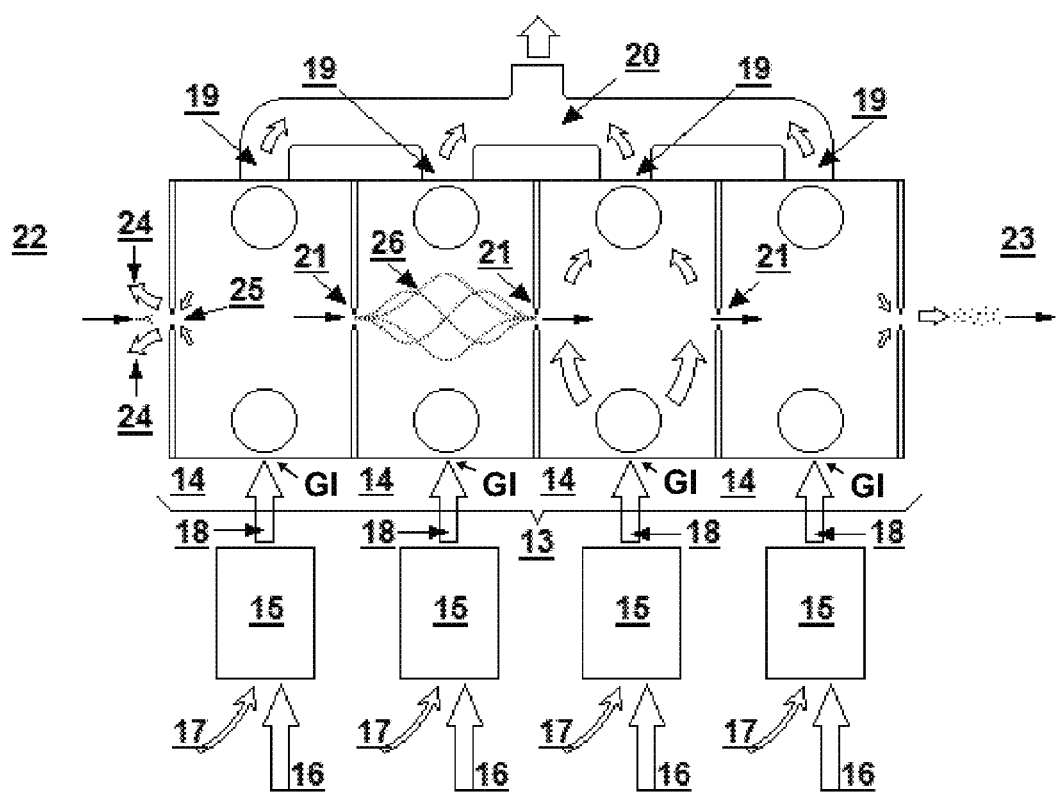
FIG. 3 illustrates schematically a set of ion mobility analyzers in accordance with the subject invention in which the gasses and dopants are continuously provided, which incorporates a set of secondary outlets that communicate through a secondary outlet collector, such that the pressure drop between each ion mobility analyzer is reduced, and where the concentrations of the flow gasses and dopants introduced in each ion mobility analyzer is previously controlled in a set of dopant mixer chambers. In this figure, each ion mobility analyzer is a VEFMA, but any ion mobility analyzer of the type that produces a continuous output of selected ions can be also used for the purposes of the present invention.

FIG. 3 illustrates schematically a multistage ion mobility analyzer, which may be in the form of a VEFMA, (13) in accordance with the present invention. As will be recognized by those skilled in the art, the principles described related hereto are equally applicable to other ion mobility analyzers arranged in series, including FAIMS and DMA. The ion mobility analyzer (13) allows for selectively introducing different gasses and dopants in each stage (14). At least one mixer (15) is provided which may be used to mix at least one gas (16) and at least one dopant (17) to produce at least one flow of gas/dopant mixture (18). A plurality of mixers (15) may be provided, in one-to-one correspondence with the stages (14), to control the concentrations of gasses (16) and dopants (17) of the gas (18) inputted into each stage (14) through secondary gas inlets (G1). This allows for selective control over introduction of different types and concentrations of gases and dopants into the stages (14), including providing no introduction to a particular stage (14) at a given time. A mixer (15) may be associated with one or more of the stages (14), understanding that the same gas/dopant mixture will be provided for the associated stages (14).

A secondary outlet of gas (19) is provided for each stage, and a low-pressure-drop outlet gas collector (20) preferably communicates with all of the secondary outlets (19), such that the pressure drop between each stage (14) is minimized, and such that the passage of gasses and dopants from one stage to the others through the intermediate inlets and outlets of ions (21), which communicate the different stages so as to transmit the ions, is minimized. Alternatively, the secondary outlets (19) may be each separately exhausted or exhausted in various combinations with the outlet gas collector (20) being manifolded with only particular secondary outlets (19).

In the embodiment of the present invention depicted in FIG. 3, all stages (14) share a common pressure, which can be different from the pressure upstream (22) and downstream (23) of the first and last stages (14), respectively. The pressure drop between the first stage (14) and the upstream region (22), produces a flow of counterflow gas (24), which sweeps the neutral contaminants away from the ion mobility analyzer (13) and precludes the entrance of contaminants produced by the ion source into the ion mobility analyzer (13). In one preferred embodiment of the present invention, ions produced by the ion source enter the first stage (14) through an inlet slit or orifice (25), and only ions with the selected mobility in the gas and dopants of the first stage reach the slit (21) communicating the first and the second stages (14). Mobility preselected ions enter the second stage through the slit or orifice (21), and only the ions with the desired mobility in the mixture of gasses and dopants of the second stage (18), reach the next slit or orifice (21). For simplicity, the trajectories of the selected ions (26) are depicted in FIG. 3 only in the second stage, but the trajectories of selected ions are similar in the rest of the stages. Selected ions are delivered continuously after passing through at least two stages (Note that FIG. 3 illustrates four stages, but any other number higher than two, including two, would be suitable for the purposes of the present invention). In each subsequent stage, the mobility of the ions is further selected in a variety of gases and dopants, which increase the orthogonality of the measurements, and finally, the selected ions reach the outlet slit. Here a pressure drop between the ion mobility analyzer (13) and the downstream region (23) produces a flow of gas, which pushes the selected ions forward (Note that ions can also be pushed in addition to, or alternatively to, by means of electric fields, which are also included in the present invention), thereby producing a continuous output of ions selected according to their mobilities in a variety of gases and dopants mixtures, which provide a very high separation capacity. Although FIG. 3 depicts a VEFMA, other ion mobility analyzers may be used which are of the mobility filter type that produces a continuous output of selected ions, such as FAIMS and DMA, and they are also included in the present invention.

In one embodiment of the present invention, two VEFMA stages are utilized (US 20100243883). In this embodiment of the present invention, a different mixture of gases and dopants is introduced in each stage. The deflector electric field of all stages is provided at the same frequency and with different angular offsets in order to eliminate the pulsed output produced by each 2D-VEFMA, as described in US 20100243883. Because the frequency of operation of all stages is the same, the selected ions must travel at the same velocity, which is given by the frequency of the deflector electric field, through each VEFMA stage. Although ions have different mobilities in each stage, a different axial voltage of each stage (the voltage between the inlet and the outlet of the stage) is utilized. As a result, ions travel at the same speed through all VEFMA stages. As a result, the assembly of the present invention allows for the elimination of the pulsed signals produced by 2D-VEFMA, at the same time that it also enables the measurement of the mobility though a sequence of different mixtures of gasses and dopants.

Figure 4:
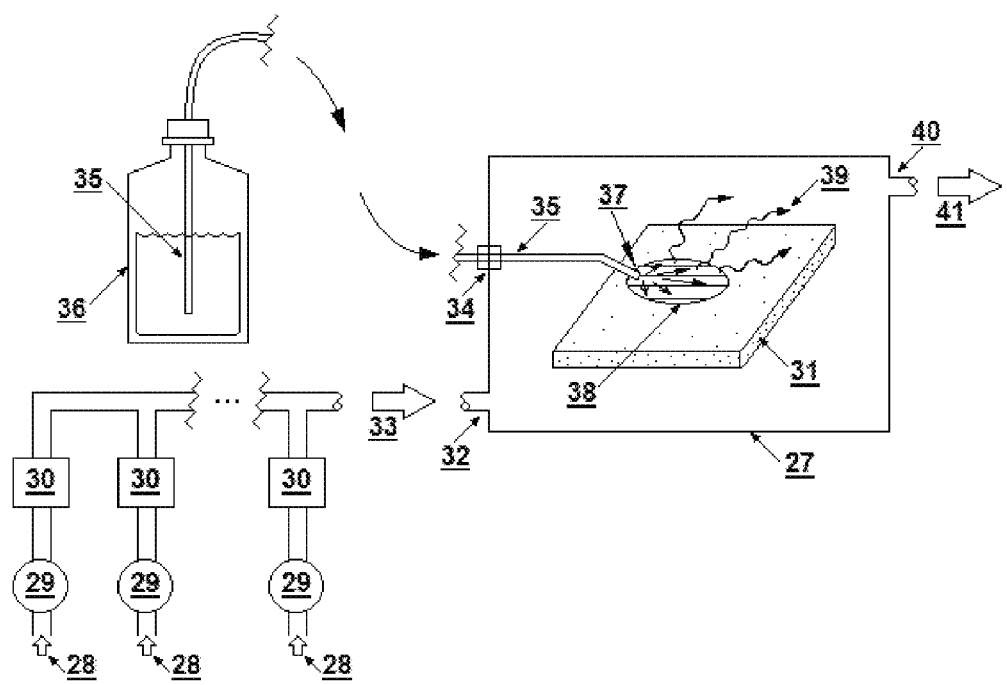
FIG. 4 illustrates schematically a mixer chamber useable with the subject invention that incorporates means to control the concentration of gases and liquid dopants.

FIG. 4 illustrates schematically one embodiment of the system described in this invention to control the concentration of gases and dopants in each ion mobility analyzer, in which the gas is continuously renewed, i.e., provided, according to the present invention. The different gases and dopants are introduced at a controlled volumetric flow in a mixing chamber (27). The mixing chamber (27) may be included in the mixer (15) described above. Gases and dopants can be inputted into the mixing chamber (27) either in the gas phase or in the liquid phase. In one embodiment of the present invention, in which at least one dopant is inputted in the liquid phase into the mixing chamber, each gas (28) is introduced through a valve (29) and a flow meter (30), the concentration of each gas is therefore proportional to the total volumetric flow entering in the mixing chamber (27). The mixing chamber (27) may also contain a porous material (31), and incorporate an inlet (32) to introduce the gases (33) and a port (34) to introduce a capillary (35), though which the liquid dopants, which are previously mixed in a reservoir (36), are introduced at a controlled volumetric flow rate (for instance, by pressurizing the liquid reservoir and producing a Poiseuille flow through the capillary, or by means of a pump of liquid, or by means of a syringe pump, or by any other means to control a small flow of liquid, which are known by those skilled in the art). The tip (37) of the capillary (35) is in contact with the porous material (31), such that the liquid dopants wet the porous material (31) in a continuous fashion that avoids the formation of droplets, which would otherwise lead to a time varying dopant concentration. Within the mixing chamber (27), the liquid dopants wet the porous material, produce a stain (38), and pass to the gas phase in the form of dopant vapors (39). In the equilibrium, the stain (38) reaches a diameter for which convection and evaporation of the liquids compensate for the liquid flow introduced through the capillary (35). With this embodiment of the present invention, in order to increase or decrease the concentration of dopants, it is necessary to increase or decrease the amount of liquid inputted in the porous material (31), and the stain automatically adapts its size until a new equilibrium is reached. Under this condition, the evaporation of dopants is steady and equal to the inputted flow of liquid. Once this steady state is reached, the concentrations of dopants and gases are constant and determined by the ratio of the flow of dopants over the flow of gases, each of which can be controlled independently. In the present invention, one mixer is required for each mobility stage in which dopants are introduced. The mixing chamber also has an outlet (40) that communicates with each ion mobility analyzer (14), and which serves to guide the mixtures of gases and dopants of controlled concentrations (41) toward the corresponding ion mobility analyzer. The mixture (41) may be emitted from the mixer (15) as the flow of gas/dopant mixture (18) described above.

Operation of Said Sequence of Ion Filters:

In one embodiment of the present invention, at least one of the ion mobility analyzers is a scannable filter (which means that it produces a continuous output of mobility selected ions), wherein said scannable ion mobility filter can be operated also in transparent mode. DMA and VEFMA are scannable ion mobility analyzers but some major differences make each technological approach suitable for different applications: DMA have shown very high transmission (to date, DMA has a higher transmission than that of the VEFMA, although it is expected that the transmission of the VEFMA will be increased as the design is more refined), but DMA cannot operate in transparent mode, while VEFMA can.

One embodiment of the new invention utilizes a VEFMA (which is taught in US 20100243883, the contents of which are incorporated herein by reference). In the new invention, by switching off the deflection voltages, said VEFMA is operated in transparent mode.

In the present invention, a VEFMA comprising two stages, in which their respective deflector electric fields operate in quadrature, can be operated in different ways. Some of these modes of operation are a novel aspect of the present invention, and they are explained in this description of the invention:

IMS mode: As described in US 20100243883, transversal modulation with two stages eliminates the pulsed output that leads to high background levels. The IMS mode requires operating the two stages with the same voltages, the same scannable frequency, and the same gases.

IMS-IMS mode: This mode of operation requires using two different gases. Although the mobility might differ from Stage 1 to 2, the electric velocities of the ions can be equated by changing the electric field strength in each stage. In these circumstances, the same frequency can be utilized to selectively pass the selected ions in both stages and to eliminate the pulsed background. In the IMS-IMS mode, the voltage AV2 and frequency of the oscillating electric fields are controlled, and ions are continuously selected according to their mobility in two different mixtures of gases.

Partially transparent mode: This mode is not described in US 20100243883, and it is considered a new contribution of this invention. IMS-IMS mode is the most selective, but tandem mobility scans are time-consuming. The possibility to operate at least one stage in transparent mode (allowing for the passage of all ions through said stage) allows the user to quickly identify the mobility in the other stages before proceeding to a deeper examination. This is achieved in one embodiment of the present invention by applying only the DC components of the voltage to the deflector electrodes, such that the oscillating electric field is eliminated in said stage, while applying the oscillating voltages in the other stages. Partially transparent modes can be utilized to quickly identify ion mobilities in each stage of the VEFMA by scanning the frequency of operation and measuring the output of the VEFMA.

Fully transparent mode: By applying only the DC components of the voltages, such that the deflector electric fields are eliminated, all ions produced by the ion source are directly driven through the VEFMA towards the ion detector or the MS, and no mobility selection is performed. This mode of operation allows the user to perform only MS analysis.

In one embodiment of the present invention, the identification of the mobilities and the mass of an ion in a sequence of ion mobility analyzers coupled with a triple quadrupole would comprise the following steps: in order to calibrate the first quadrupole, a known amount of substance is introduced in the instrument by the operator, the third quadrupole and the stages of said sequence of ion mobility analyzers are operated in transparent mode (allowing the passage of all ions), the first quadrupole is scanned so as to produce a spectrum, and the mass of the precursor ion is identified in this first spectrum. The mobility in each stage of the sequence of ion mobility analyzers is identified by operating the rest of the stages in transparent mode and by scanning the mobility of the stage under study. And finally, the masses of the fragments in the third quadrupole are identified by allowing the passage of only the precursor ions (preselected by at least the sequence of ion mobility analyzers, or the first quadrupole), and scanning the masses in the third quadrupole so as to produce a spectrum.

In a tandem sequence of ion filters in which each filter can be operated in transparent mode, the time required to identify the filtering parameter is the sum of the time required in each filter. Accordingly, if the spectrum of each ion mobility analyzers requires 200 points, and each point requires 50 ms, the identification of the mobility in each VEFMA stage takes 5 seconds, and the identification of the set of filtering parameter in a tandem multistage VEFMA coupled with a triple quadrupole is always very low (2 minutes for the triple quadrupole and 5 seconds if a VEFMA with one stage is used and N·5 seconds if N stages of VEFMA are used). This method of identifying the filtrating parameters in each mobility filter, in which each filter (comprising at least one mobility filter) can be operated in transparent mode, is new, and it is a part of the present invention. This method is particularly suitable when said sequence of ion mobility analyzers is a multistage VEFMA, but it can also by applied with other set of ion filters in which at least one of the filters is a scannable ion mobility filter which can be operated in transparent mode, and these configurations are also part of the present invention.

Proof of Principle:

In a set of preliminary tests designed to evaluate the viability of the present invention, a first demonstrator was developed that incorporated two VEFMA stages, and that also incorporated the dopant and gas mixing system described in the present invention with respect to FIG. 4. The objective of this study was to prove viability of the present invention by proving the functional viability of the two-stage VEFMA architecture, and to prove that it could be coupled with a Mass Spectrometer (MS). The two stages were operated in quadrature, and we coupled them with an API-MS (API3200, from ABSciex). In order to investigate the different enhanced separation capacity of the new architecture, a set of tetra-alkyl ammonium ions was utilized, with nitrogen (as produced by a N2 generator) being introduced in one of its stages, and N2 doped with 2-propanol being introduced in the second stage.

Figure 5:
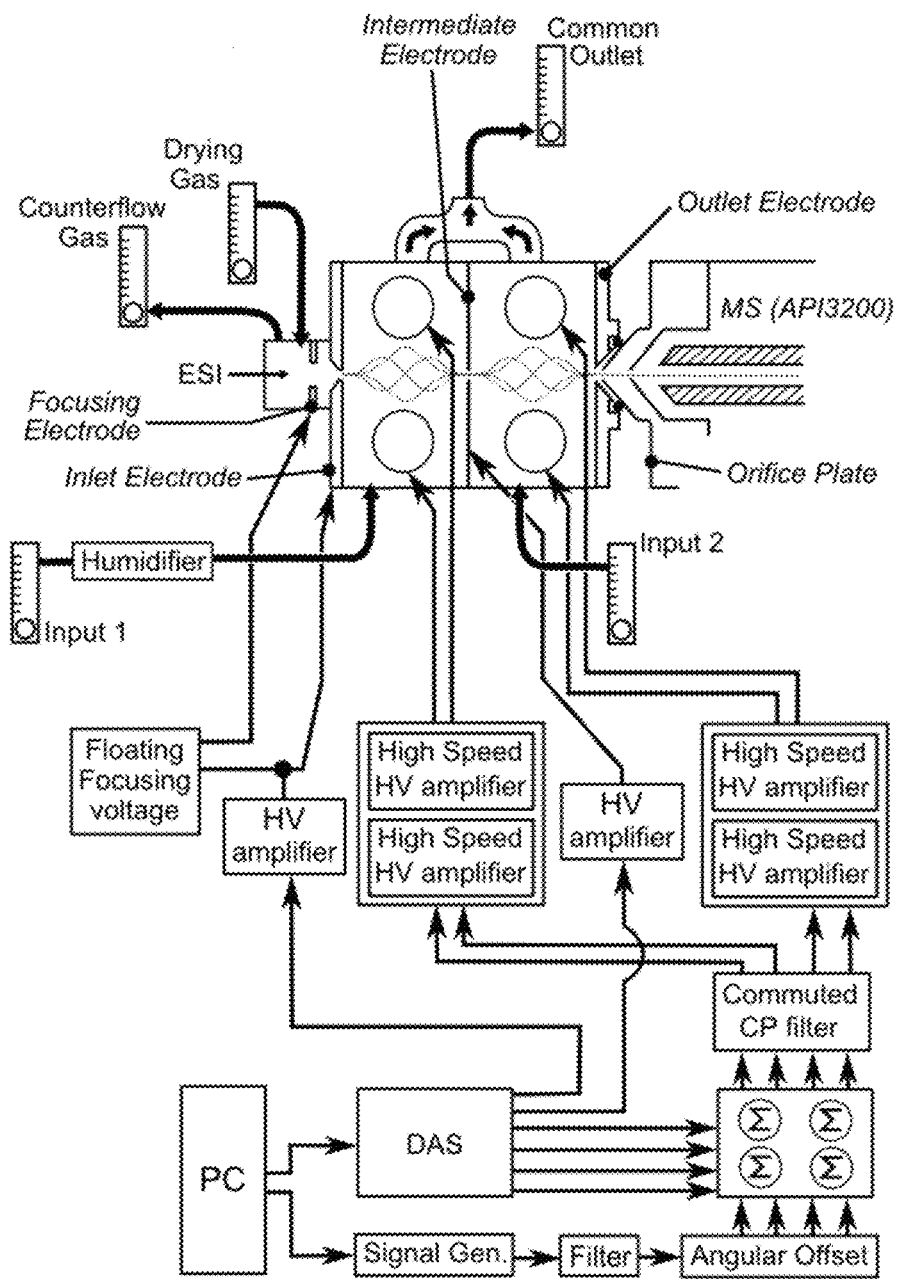
FIG. 5 illustrates schematically a two-stage VEFMA coupled with an MS experimental set-up including an ESI source, focusing electrode, two stages VEFMA, deflector electrodes, inlet and intermediate electrodes, and outlet electrode that matches the inlet orifice of an API-MS. The figure also illustrates the architecture of the flow controls and the electronics (low voltage and high voltage) used to control the two-stage VEFMA.

FIG. 5 shows schematically the architecture of the VEFMA used in this study. The VEFMA was composed of two symmetrically designed insulator boxes, the first (Stage 1) housing the inlet electrode, each housing two cylindrical deflector electrodes, and the second (Stage 2) housing the outlet electrode. Each stage was 5 cm long, the diameter of the deflector electrodes was 3 cm, and their centers were 7 cm apart. The inlet electrode incorporated a gas-tight nano-electrospray (nanoESI) chamber and a focusing electrode that guided the ionic flow towards the inlet slit. A thin plate (0.5 mm thick) separated the two stages and allowed ions to be transferred through what we termed an intermediate slit. The outlet electrode incorporated a slit which was elongated on the side receiving the selected ions, and which became a rounded orifice on the opposite side of the outlet electrode so as to better fit the inlet of the following API-MS. The most downstream side of the outlet electrode was shaped to fit the 'Orifice Plate' of an API 3200 (AB-Sciex), and incorporated an O-ring which ensured that the gas sampled by the API system was drawn only from the VEFMA. The VEFMA was easily assembled with the API-MS by removing the original ion source and the curtain plate, and installing the VEFMA, which fitted with the original housing of the ion source, instead. This operation took no longer than 5 minutes, and it didn't require to interrupt the vacuum pumps of the MS. Two lateral inlets, which were equipped with laminarizing meshes in order to prevent turbulence, served to introduce a controlled flow of gas into each VEFMA chamber. Ions reaching the outlet slit were directly carried by the flow toward the vacuum side of the MS, while a counterflow gas exits through the inlet slit so as to prevent droplets from entering the analyzer. The two chambers were also equipped with two secondary outlets, which communicate toward a common outlet, and which have a low pressure drop. These outlets served to balance the pressure between the two chambers so as to ensure that no disrupting jets were formed in the intermediate slit. As a result, ions are transferred through the intermediate slit relying solely on the electric fields.

Pure nitrogen (produced by means of a nitrogen generator, which provided 99.5% purity) was introduced in Stage 2, which communicated directly with the MS, while the gas introduced in Stage 1 was previously doped with 2-propanol in a humidifier, which allowed the concentration to be controlled in the range from 0% to 2%. A flow of heated and dry gas was also introduced in a gas tight electrospray chamber, which communicated with the VEFMA inlet slit in order to assist the desolvation of ions. The electrospray chamber also incorporated a focusing electrode, which was shaped as a plate with a wide slit, and which was positioned between the VEFMA inlet slit and the tip of the electrospray in order to guide the ions forming in the spray towards the inlet slit.

The voltages required by the inlet electrode and the intermediate electrode were supplied by two Applied Kilovolts high voltage amplifiers (HVA), while the outlet electrode was electrically connected with the MS inlet. The Deflector Electrode voltages (DE1 through DE4) were supplied by four Matsusada high voltage and high speed amplifiers (HVHSA). The focusing and the electrospray voltages were provided by two manually controlled EMCO power supplies that floated above the inlet electrode voltage.

A signal generator produced a wave signal which was first filtered to eliminate its DC component and then fed to an angular offset generator [23], which provided four waves with the same amplitude and frequency, but with 90° offsets. These waves were then biased with four DC signals produced by a Data Acquisition System (DAS), which also generated the DC signals used to command the axial voltages. Finally, each wave signal was passed through a switch (termed here the AC/DC switch) that allowed the user to either pass the complete signal, or to eliminate the time varying component of the signals by means of a set of filters before commanding the HVHSA. These filters allowed to selectively switching on and off the oscillating voltage of each deflector electrode. The signal generator and the DAS were controlled by a PC which incorporated the SW required to control the frequencies, the wave amplitude, and the DC component of each electrode. The signals were acquired by the MS, and signal versus time data were stored in a second PC controlling the MS. While the frequency and the voltage of operation of the VEFMA were controlled in the first PC, in which the VEFMA operational parameters (frequency and voltages) were also stored as a function of time. Finally, spectra were reconstructed upon synchronization of the data stored in each PC.

A solution of tetra-alkyl ammonium (TAA) salts of different chain length, which ranged from tetrapropyl (C3) to tetradodecyl (C12), was electrosprayed (Methanol-Water 9:1 in volume, and 10 micro-molar of each salt). The frequency and the voltages of the VEFMA electrodes were swept, the signal produced by each type of ion was acquired by the MS, and the corresponding spectra were later reconstructed and analyzed in order to evaluate the performance of the new architecture.

Figure 6A:
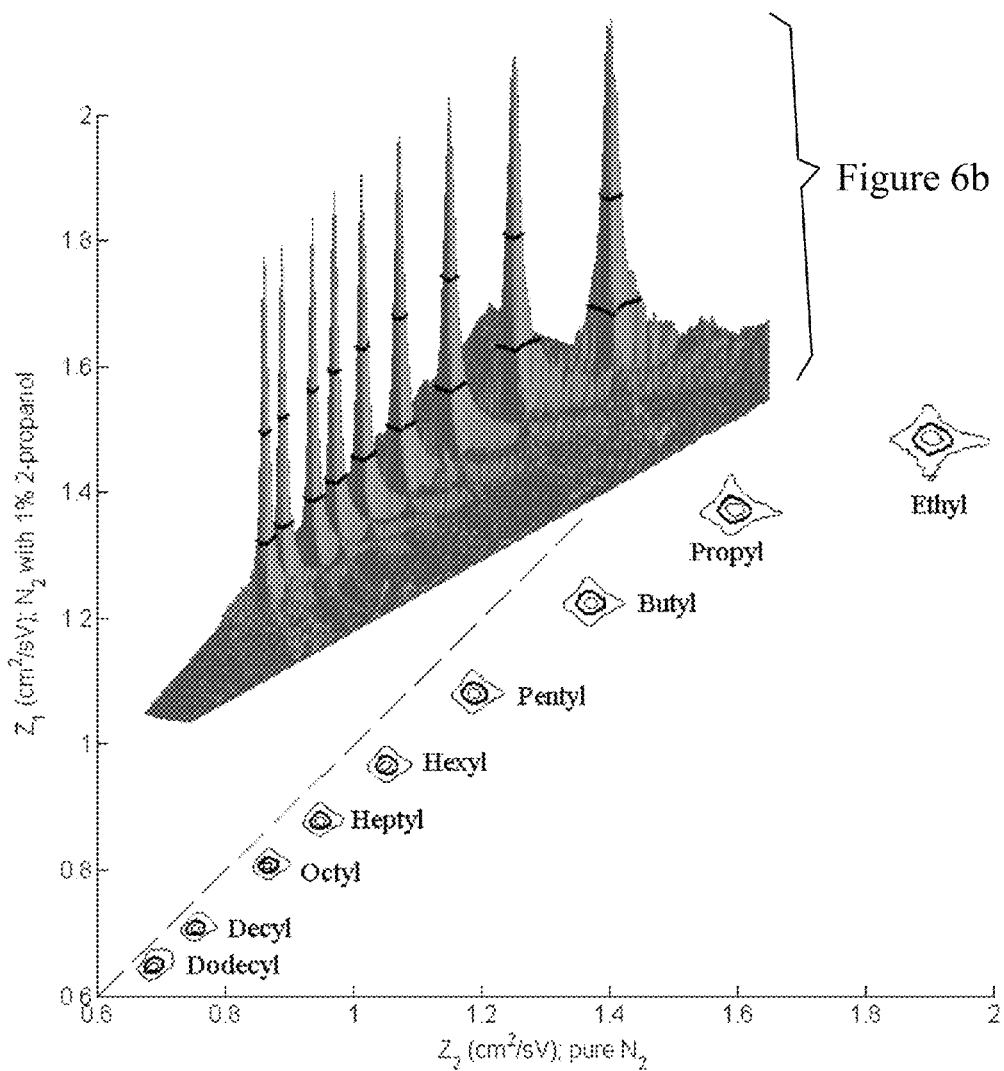
FIG. 6a is a contour plot of the IMS-IMS spectra of the tetra-alkyl ammonium ions, the dashed line shows where the peaks would appear if the mobility in the two stages was equal.

FIGS. 6a and 6b illustrate a set of normalized IMS-IMS spectra (each peak correspond to the signal produced by one type of TAA ions; FIG. 6a is a contour view, and. the insert, FIG. 6b, is a three dimensional projection of the same data), where both the frequency of operation and the voltage of the intermediate electrode were scanned, and where the MS was utilized to sequentially analyze the signal produced by the different tetra-alkyl-ammonium ions. In order to facilitate the interpretation of the spectra, the f-AE2 domain was transformed to the K1-K2 domain (mobility in stage 1 and mobility in stage 2) under the hypothesis that the mobility in each stage was inversely proportional to its axial voltage, and proportional to the frequency, and where proportionality constant was chosen so that the mobility of tetra-heptyl ammonium (THA+) ions in N2 and at room temperature and pressure was 0.97 cm2/sV.

These experiments showed that the variations of the mobility are very strong, enough to be easily distinguished, and they suggested that the IMS-IMS approach with a combination of dry gas and doped gas provides an enhanced separation capacity, where the mobility shifts are strong enough to be easily measured with relatively high resolving powers.

Figure 7:
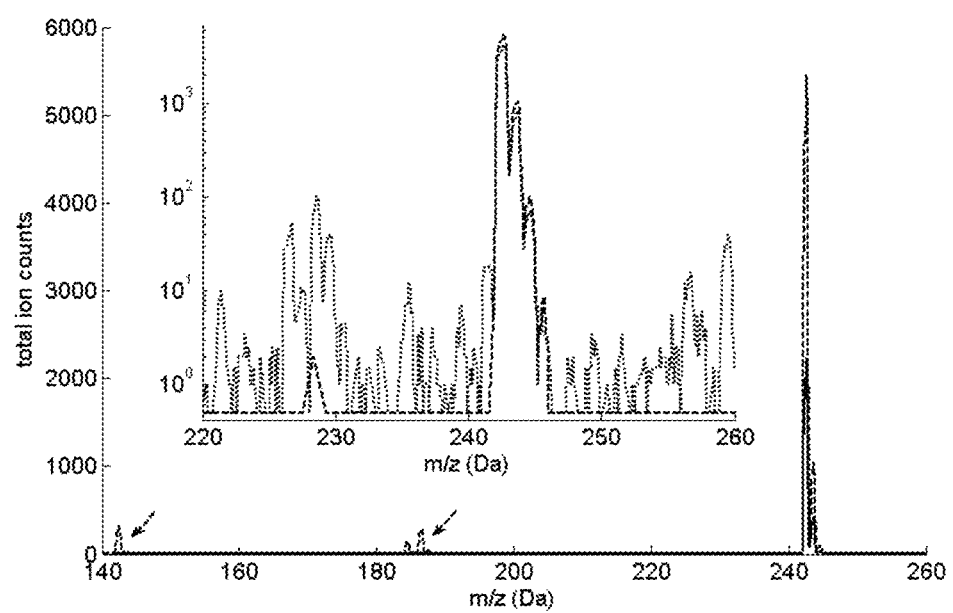
FIG. 7 shows the MS spectra of an electro-sprayed solution. The insert shows the MS spectra when the VEFMA was operated in transparent mode (dotted line), and when the VEFMA was operated in IMS mode (dashed line). The main figure shows the MS spectra when the VEFMA was operated in IMS mode (dashed line) and in IMS-IMS mode (solid line).

In order to test the separation capacity of the new architecture as a pre-filtering device for MS, we compared the mass spectra acquired when the VEFMA was operated in transparent mode (dotted line of the insert of FIG. 7; no oscillating electric fields were applied) and when it was operated as a single IMS filter (dashed line of the insert of FIG. 7; the frequency of the VEFMA was set to selectively pass only the mobility of tetra-butil-ammonium (TBA) ions, and the same type of gass was introduced in the two stages). We also compared these results with a mass spectra acquired when the VEFMA was operated as an IMS-IMS pre-filter (solid line of FIG. 6b; one stage was doped with 1% 2-propanol, and the frequency and the voltage of the intermediate electrode were set to pass the mobility of TBA in each stage). The insert of FIG. 7 illustrates a detail of the neighboring masses of the first spectra in logarithmic scale. This figure shows that the IMS pre-filter cleans the mass spectra while maintaining the signal of the selected ions very close to the original level. However, the IMS mode did not eliminate all species of the spectrum: we found that tetra-propyl-ammonium ions (186 Da) and an unknown contaminant (142 Da) were not eliminated in the VEFMA. In the last part of the experiment, we found that the addition of the extra separation dimension provided by the addition of the dopant 2-propanol to the second stage totally eliminated the undesired ions. These results illustrate how the improved orthogonality of these measurements increase the separation capacity of the new analyzer.

Figure 2:
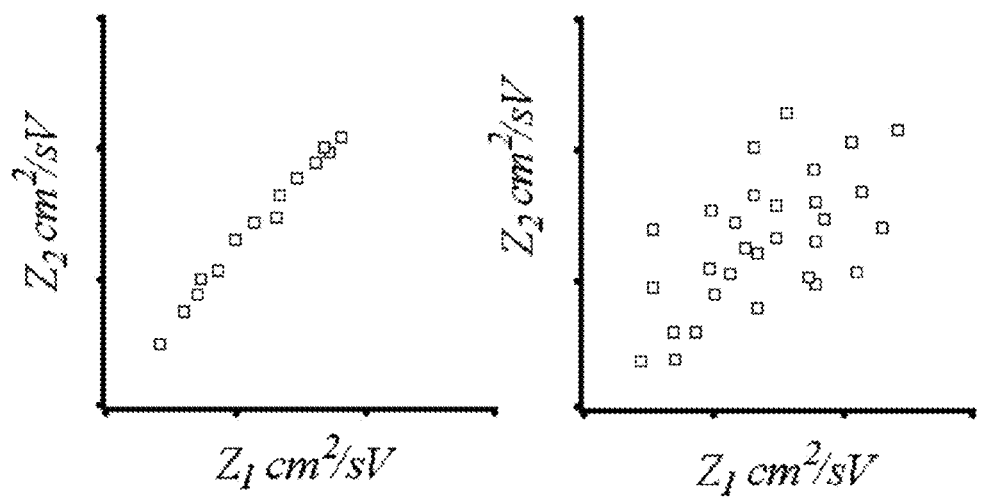
FIG. 2 illustrates schematically two sets of mobility pairs, in which each point corresponds with the pair of mobilities of a given ion in each mobility measurement stage. In the first case (left, poor orthogonality), the mobilities in the two stages are linked (the dots are not dispersed, meaning that the measurement are not orthogonal). As a result, two different types of ions, which have the same mobility in the first stage, and which thus pass together through the first stage at a given mobility (not being differentiated in the first stage), cannot be differentiated in a second stage because their mobilities in the second stage are also very similar. In the second case (right, better orthogonality), the mobilities in the two stages are not linked (the dots are dispersed, meaning that they are highly orthogonal). In this case, although two type of ions, which have the same mobility in the first stage cannot be differentiated in the first stage, they will be differentiated in the second stage.
Figure 8:
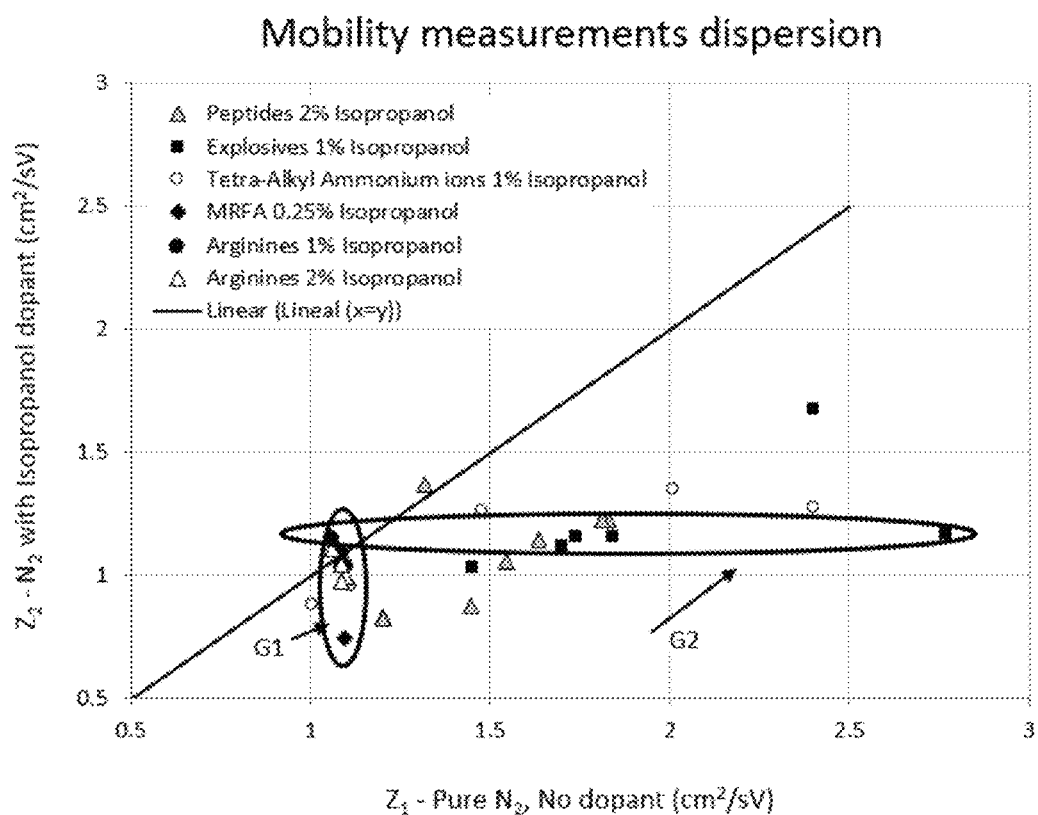
FIG. 8 shows the dispersion of the mobility pairs for a set of species that were measured with the instrument designed and tested to proof the viability of the present invention. It also illustrates how the new invention can provide an increased separation capacity by allowing the ions to be sequentially classified according to their mobility in two different mixtures of gases and dopants.

FIG. 8 shows the dispersion of the mobility measurements provided by the instrument utilized in the proof of principle studies (This figure is equivalent to that of FIG. 2, but it is based on real data. The horizontal axis is the mobility measured in the first stage of the VEFMA, and the vertical axis is the mobility measured in the second stage. Each dot corresponds with a known species). This plot summarizes the measured mobilities that have been acquired for the set of Peptides (Angiotensin II, Gly-Tyr, Leu encephalin, Met encephalin, al-Tyr-Val, Met-Arg-Phe-Ala (MRFA)), a set of explosives (EGDN, DNT, RDX, Nitroglicerine, TNT), a set of Tetra-Alkyl Ammonium ions (Tetra-methyl Ammo. Ionide (TMAI), Tetra-ethyl Ammo. Bromide (TEAB), Tetra-buthyl Ammo. Ionide (TBAI), Tetra-hexyl Ammo. Bromide (THexAB), Tetra-hepthyl Ammo. Bromide (THAB), and a set Arginines (Arginine, Symmetric dimethylarginine (SDMA), Asymemetric dimethylarginine (ADMA), L-Homoarginine (HA), N-monomethylarginine (NMMA)), and (MRFA).

FIG. 8 illustrates the increased separation capacity of the new approach. It is clear that the different dots are very disperse and that they do not follow a common trend. This figure also illustrates the advantage of being able to simultaneously separate ions in two different mixtures of gases and dopants. For instance, for this particular mixture of species, an ion mobility analyzer measuring the mobility only in clean Nitrogen would easily be able to separate the species of the group G2 (labeled in FIG. 8), but it would not be able to distinguish the majority of the species of the group G1 (labeled also in FIG. 8). The species of the group G1 could be resolved by introducing a dopant (isopropanol, in this particular case), but then the ion mobility analyzer which could separate the species of the group G1 after incorporating the dopant would not be able to separate the species of the group G2. In contrast, the instrument described in the present invention can separate all these species because it can measure with dopants and without dopants simultaneously.

CITED PUBLICATIONS

1. Gotts, N. G., von Helden, G. & Bowers, M. T. Carbon cluster anions: structure and growth from C5- to C62-. *Int. J. Mass Spectrom. Ion Process.* 149-150, 217-229 (1995).
2. Bohrer, B. C., Merenbloom, S. I., Koeniger, S. L., Hilderbrand, A. E. & Clemmer, D. E. Biomolecule analysis by ion mobility spectrometry. *Annu. Rev. Anal. Chem. Palo Alto Calif.* 1, 293-327 (2008).
3. Jarrold, M. F. Peptides and proteins in the vapor phase. *Annu. Rev. Phys. Chem.* 51, 179-207 (2000).
4. Koeniger, S. L., Merenbloom, S. I. & Clemmer, D. E. Evidence for many resolvable structures within conformation types of electrosprayed ubiquitin ions. *J. Phys. Chem. B* 110, 7017-7021 (2006).
5. Shvartsburg, A. A., Li, F., Tang, K. & Smith, R. D. Characterizing the structures and folding of free proteins using 2-D gas-phase separations: observation of multiple unfolded conformers. *Anal. Chem.* 78, 3304-3315 (2006).
6. E. A. Mason, H. E. R. Theory of plasma chromatography/ gaseous electrophoresis. Review. *Anal. Chem.* 47, 970-983 (1975).
7. Eiceman, G. A. & Karpas, Z. *Ion Mobility Spectrometry, Second Edition.* (CRC Press, 2004).
8. Hoaglund-Hyzer, C. S., Counterman, A. E. & Clemmer, D. E. Anhydrous protein ions. *Chem. Rev.* 99, 3037-3080 (1999).
9. Valentine, S. J. et al. Toward plasma proteome profiling with ion mobility-mass spectrometry. *J. Proteome Res.* 5, 2977-2984 (2006).
10. Taraszka, J. A. et al. Proteome profiling for assessing diversity: analysis of individual heads of *Drosophila melanogaster* using LC-ion mobility-MS. *J. Proteome Res.* 4, 1238-1247 (2005).
11. Ruotolo, B. T. et al. Evidence for macromolecular protein rings in the absence of bulk water. *Science* 310, 1658-1661 (2005).

12. Tang, K. et al. High-sensitivity ion mobility spectrometry/mass spectrometry using electrodynamic ion funnel interfaces. *Anal. Chem.* 77, 3330-3339 (2005).
13. Belov, M. E., Buschbach, M. A., Prior, D. C., Tang, K. & Smith, R. D. Multiplexed ion mobility spectrometry-orthogonal time-of-flight mass spectrometry. *Anal. Chem.* 79, 2451-2462 (2007).
14. Merenbloom, S. I., Glaskin, R. S., Henson, Z. B. & Clemmer, D. E. High-Resolution Ion Cyclotron Mobility Spectrometry. *Anal. Chem.* 81, 1482-1487 (2009).
15. Glaskin, R. S., Valentine, S. J. & Clemmer, D. E. A scanning frequency mode for ion cyclotron mobility spectrometry. *Anal. Chem.* 82, 8266-8271 (2010).
16. Merenbloom, S. I., Flick, T. G. & Williams, E. R. How hot are your ions in TWAVE ion mobility spectrometry? *J. Am. Soc. Mass Spectrom.* 23, 553-562 (2012).
17. Shvartsburg, A. A. & Smith, R. D. Fundamentals of Traveling Wave Ion Mobility Spectrometry. *Anal. Chem.* 80, 9689-9699 (2008).
18. Smith, D. et al. Deciphering drift time measurements from travelling wave ion mobility spectrometry-mass spectrometry studies. *Eur. J. Mass Spectrom.* 15, 113 (2009).
19. Purves, R. W., Guevremont, R., Day, S., Pipich, C. W. & Matyjaszczyk, M. S. Mass spectrometric characterization of a high-field asymmetric waveform ion mobility spectrometer. *Rev. Sci. Instrum.* 69, 4094-4105 (1998).
20. Shvartsburg, A. A., Tang, K. & Smith, R. D. Optimization of the design and operation of FAIMS analyzers. *J. Am. Soc. Mass Spectrom.* 16, 2-12 (2005).
21. Guevremont, R. High-field asymmetric waveform ion mobility spectrometry: a new tool for mass spectrometry. *J. Chromatogr. A* 1058, 3-19 (2004).
22. Barnett, D. A., Belford, M., Dunyach, J.-J. & Purves, R. W. Characterization of a temperature-controlled FAIMS system. *J. Am. Soc. Mass Spectrom.* 18, 1653-1663 (2007).
23. Shvartsburg, A. A., Tang, K. & Smith, R. D. Modeling the resolution and sensitivity of FAIMS analyses. *J. Am. Soc. Mass Spectrom.* 15, 1487-1498 (2004).
24. Shvartsburg, A. A., Li, F., Tang, K. & Smith, R. D. High-resolution field asymmetric waveform ion mobility spectrometry using new planar geometry analyzers. *Anal. Chem.* 78, 3706-3714 (2006).
25. Shvartsburg, A. A. & Smith, R. D. Scaling of the resolving power and sensitivity for planar FAIMS and mobility-based discrimination in flow- and field-driven analyzers. *J. Am. Soc. Mass Spectrom.* 18, 1672-1681 (2007).
26. Schneider, B. B., Covey, T. R., Coy, S. L., Krylov, E. V. & Nazarov, E. G. Chemical Effects in the Separation Process of a Differential Mobility/Mass Spectrometer System. *Anal. Chem.* 82, 1867-1880 (2010).
27. Krylov, E. V. et al. Selection and generation of waveforms for differential mobility spectrometry. *Rev. Sci. Instrum.* 81, 024101 (2010).
28. Schneider, B., Covey, T., Coy, S., Krylov, E. & Nazarov, E. Control of chemical effects in the separation process of a differential mobility mass spectrometer system. *Eur. J. Mass Spectrom.* 16, 57 (2010).
29. Krylov, E. V. & Nazarov, E. G. Electric field dependence of the ion mobility. *Int. J. Mass Spectrom.* 285, 149-156 (2009).
30. Shvartsburg, A. A. & Smith, R. D. Ultrahigh-resolution differential ion mobility spectrometry using extended separation times. *Anal. Chem.* 83, 23-29 (2011).
31. Coy, S. L. et al. Detection of Radiation-Exposure Biomarkers by Differential Mobility Prefiltered Mass Spectrometry (DMS-MS). *Int. J. Mass Spectrom.* 291, 108-117 (2010).
32. Schneider, B. B., Covey, T. R., Coy, S. L., Krylov, E. V. & Nazarov, E. G. Planar differential mobility spectrometer as a pre-filter for atmospheric pressure ionization mass spectrometry. *Int. J. Mass Spectrom.* 298, 45-54 (2010).
33. Rus, J. et al. IMS-MS studies based on coupling a differential mobility analyzer (DMA) to commercial API-MS systems. *Int. J. Mass Spectrom.* 298, 30-40 (2010).
34. Hogan, C. J. & Fernandez de la Mora, J. Ion-pair evaporation from ionic liquid clusters. *J. Am. Soc. Mass Spectrom.* 21, 1382-1386 (2010).
35. Hogan Jr, C. J. & Fernandez de la Mora, J. Tandem ion mobility-mass spectrometry (IMS-MS) study of ion evaporation from ionic liquid-acetonitrile nanodrops. *Phys. Chem. Chem. Phys.* 11, 8079 (2009).
36. Hogan, C. J., Ruotolo, B. T., Robinson, C. V. & Fernandez de la Mora, J. Tandem Differential Mobility Analysis-Mass Spectrometry Reveals Partial Gas-Phase Collapse of the GroEL Complex. *J. Phys. Chem. B* 115, 3614-3621 (2011).
37. Hogan, C. & de la Mora, J. Ion Mobility Measurements of Nondenatured 12-150 kDa Proteins and Protein Multimers by Tandem Differential Mobility Analysis-Mass Spectrometry (DMA-MS). *J. Am. Soc. Mass Spectrom.* 22, 158-172 (2011).
38. De la Mora, J. F., de Juan, L., Eichler, T. & Rosell, J. Differential mobility analysis of molecular ions and nanometer particles. *Trac Trends Anal. Chem.* 17, 328-339 (1998).
39. Merenbloom, S. I., Koeniger, S. L., Valentine, S. J., Plasencia, M. D. & Clemmer, D. E. IMS-IMS and IMS-IMS-IMS/MS for separating peptide and protein fragment ions. *Anal. Chem.* 78, 2802-2809 (2006).
40. Koeniger, S. L. et al. An IMS-IMS Analogue of MS-MS. *Anal. Chem.* 78, 4161-4174 (2006).
41. Koeniger, S. L., Bohrer, B. C., Valentine, S. J. & Clemmer, D. E. Improving the Efficiency of IMS-IMS by a Combing Technique. *Anal. Chem.* 80, 1918-1927 (2008).
42. Merenbloom, S. I., Bohrer, B. C., Koeniger, S. L. & Clemmer, D. E. Assessing the peak capacity of IMS-IMS separations of tryptic peptide ions in He at 300 K. *Anal. Chem.* 79, 515-522 (2007).
43. Bohrer, B. C. & Clemmer, D. E. Shift Reagents for IMS-IMS-MS Analysis of Complex Peptide Mixtures: Evaluation of 18-Crown-6 Ether Complexes. *Anal. Chem.* 83, 5377-5385 (2011).
44. Li, H., Bendiak, B., Siems, W. F., Gang, D. R. & Hill, H. H. Carbohydrate Structure Characterization by Tandem Ion Mobility Mass Spectrometry (IMMS)2. *Anal. Chem.* 85, 2760-2769 (2013).
45. McMurry, P. H. & Rader, D. The Tandem Differential Mobility Analyzer. *Tsi J. Part. Instrum.* 1, 3-15 (1986).
46. Bohrer, B. C. & Clemmer, D. E. Shift Reagents for IMS-IMS-MS Analysis of Complex Peptide Mixtures: Evaluation of 18-Crown-6 Ether Complexes. *Anal. Chem.* 83, 5377-5385 (2011).

What is claimed:

1. An apparatus to separate ions simultaneously in different mixtures of gases and dopants with an enhanced separation capacity and with an improved transmission of ions, said apparatus comprising at least two ion mobility analyzers, each of said ion mobility analyzers having an inlet of ions and an outlet of ions, wherein at least one among said two ion mobility analyzers is a scannable filter of the type: a Field Asymmetric Ion Mobility Spectrometer (FAIMS), a Differential Mobility Analyzer (DMA), or a Variable Electric Field Mobility Analyzer (VEFMA), for which said inlet of ions and said outlet of ions is a orifice or an slit, wherein said ion mobility analyzers are arranged in a linear sequence, having at least a first ion mobility analyzer, which receives a plurality of ions through a first inlet, and a last ion mobility analyzer which outputs a flow of selected ions through a last outlet, wherein said outlet of ions of said ion mobility analyzers, excluding said last ion mobility analyzer, serves at the same time as an inlet for the next ion mobility analyzer, and wherein ions classified in one stage are passed to a next for further classification, wherein a different mixture of gasses and dopants, which produce different shifts in the mobilities of each type of said ions, is introduced in each of said last ion mobility analyzers through a secondary inlet in each analyzer, wherein said plurality of ions is consecutively classified in said sequence of ion mobility analyzers.

2. A method to operate the apparatus of claim 1, further reducing the time required to identify the filtering parameters of a predetermined species in said analyzer of ions comprising at least one scannable ion mobility analyzer producing a continuous output of mobility selected ions, and other optional analyzers, the method comprising the steps of:

operating at least one of said ion mobility filters in transparent mode, such that all ions are transferred, and such that the effect of said other optional analyzers can be analyzed independently, scanning said filtering parameters in said other optional analyzers so as to produce a spectrum or a set of spectra of said filtering parameters, identifying said filtering parameters of said predetermined species by measuring the position of a prominent peak in said spectrum or spectra in said other optional analyzers, and scanning independently the filtering parameters of said at least one scannable ion mobility filters, such that a spectrum or a spectra of said scannable ion mobility analyzer is acquired, and identifying said filtering of said predetermined species by measuring the position of a prominent peak in said spectrum or spectra in said scannable ion mobility analyzer.

3. The method of claim 2, wherein said ion mobility analyzer is a VEFMA having an inlet and an outlet, an axial electric field and an oscillating electric field, and wherein said transparent mode is accomplished by switching off said oscillating electric field, such that all ions passing through said inlet reach said outlet.

4. The apparatus of claim 1, wherein said sequence of analyzers is a multistage VEFMA, further incorporating:

a secondary outlet in each ion mobility analyzer through which a continuous flow of gas is evacuated, and a low pressure drop secondary outlet collector that communicates said secondary outlets, and which provides a common pressure reference for all the VEFMA stages, which eliminates the convective passage of gasses and dopants from each of said ion mobility analyzers through said ion inlets and outlets communicating each ion mobility analyzer with the next, which evacuates a flow of gas, which thus enables said different mixtures of gasses and dopants to be continuously renewed, and which compensates for the diffusional passage of gasses and dopants through said inlets and outlets.

5. The apparatus of claim 4 where said set of VEFMA is a 2D-VEFMA having a different oscillating electric field and a different axial electric field in each stage, wherein said oscillating electric fields are operated at the same frequency in each of said stages, and where said oscillating electric fields of each VEFMA has a different angular offset, such that said set of VEFMA simultaneously filters ions according to their mobility in different mixtures of gases and dopants, and eliminate any pulsed output produced by each 2D VEFMA alone.

6. A system to separate ions, said system comprising:

a first stage, said first stage including an ion mobility analyzer, said first ion mobility analyzer including a first ion inlet and a first ion outlet;

a second stage, said second stage including an ion mobility analyzer including a second ion inlet and a second ion outlet, wherein said second ion inlet of said second ion mobility analyzer is in direct communication with said first ion outlet of said first ion mobility analyzer;

at least one mixer for mixing at least one gas and at least one dopant to produce at least one flow of gas/dopant mixture;

a first gas inlet and a first gas outlet located in said first stage; and, a second gas inlet and a second gas outlet located in said second stage, wherein, said at least one flow of gas/dopant mixture is selectively introducible through each of said first gas inlet and said second gas inlet to selectively and separately introduce said at least one gas/dopant mixture into said first and second stages.

7. The system of claim 6, wherein at least one of said stages is an ion mobility analyzer of the mobility filter type that produces a continuous output of selected ions.

8. The system of claim 6, further comprising a third stage including an ion mobility analyzer including a third ion inlet and a third ion outlet, wherein said third ion inlet of said third ion mobility analyzer is in direct communication with said second ion outlet of said second ion mobility analyzer.

9. The system of claim 6, further comprising:

a secondary outlet collector communicating with said first gas outlet and said second gas outlet, wherein said secondary outlet collector equates the pressure of said first ion mobility analyzer and said second ion mobility analyzer, thereby eliminating the convective passage of gases and dopants between said first and second stages, and evacuates said at least one flow of gas/dopant mixture.

10. The system of claim 6, wherein an ion flowpath is defined between said first ion inlet and said first ion outlet, and a gas flowpath is defined between said first gas inlet and said first gas outlet, said gas flowpath being transverse to said ion flowpath.

11. The system of claim 6, wherein each stage is a 2D-VEFMA with a first oscillating electric field being defined in said first stage, a second oscillating electric field being defined in said second stage, a first axial electric field being defined in said first stage, a second axial electric field being defined in said second stage, said first axial electric field and said second electric field wherein said first and said second oscillating electric fields oscillate at an equal frequency and with an angular offset of 90 degree, and wherein said equal frequency and said first and second axial electric fields are scanned to selectively transmit only said ions having the selected mobility in said first stage and in said second stage.

12. The system of claim 11, wherein said first oscillating electric field is selectively removable.

13. The system of claim 11, wherein said second oscillating electric field is selectively removable.

* * * * *